United States Patent [19]
Vines

[11] Patent Number: 5,400,803
[45] Date of Patent: Mar. 28, 1995

[54] APPARATUS FOR SUPPORT OR POSITIONAL TREATMENT

[75] Inventor: Amy B. Vines, Lisle, Ill.

[73] Assignee: Tracy Medical Resources, Inc., Lisle, Ill.

[21] Appl. No.: 921,359

[22] Filed: Jul. 27, 1992

Related U.S. Application Data

[63] Continuation-in-part of Ser. No. 733,722, Jul. 22, 1992, abandoned.

[51] Int. Cl.⁶ .............................................. A61F 13/00
[52] U.S. Cl. ........................................ 128/872; 5/494; 128/869; 128/873
[58] Field of Search ............... 128/872, 869, 873, 874, 128/875, 876; 5/494, 482, 424; 2/69.5, 75, 80

[56] References Cited

U.S. PATENT DOCUMENTS

| | | | |
|---|---|---|---|
| 1,048,033 | 12/1912 | Brown . | |
| 1,639,424 | 8/1927 | Breslin . | |
| 2,102,281 | 3/1935 | Pringle | 128/875 |
| 2,423,392 | 8/1946 | Krogh | 128/873 |
| 2,524,429 | 6/1948 | Devin | 128/873 |
| 2,758,595 | 8/1956 | Lovett | 128/134 |
| 2,863,450 | 12/1958 | Johnson | 128/874 |
| 3,323,150 | 6/1967 | Rehder | 5/336 |
| 4,657,005 | 4/1987 | Williamson | 128/134 |
| 4,672,958 | 6/1987 | Garman | 128/134 |
| 4,807,737 | 2/1989 | Harrigan | 128/874 |
| 4,858,625 | 8/1989 | Cramer | 128/872 |
| 4,860,771 | 8/1989 | Burgos | 128/872 |
| 4,862,535 | 9/1989 | Roberts | 5/494 |
| 4,911,105 | 3/1990 | Hocum | 119/96 |
| 4,989,286 | 2/1991 | Tucker | 5/482 |

*Primary Examiner*—Robert A. Hafer
*Assistant Examiner*—David J. Kenealy
*Attorney, Agent, or Firm*—Willian Brinks Hofer Gilson & Lione

[57] ABSTRACT

An article for support of an individual is disclosed which includes a body supporting member having a first portion adapted to encircle the waist of an individual, and a second portion adapted to pass through the crotch of an individual. The article for support further includes at least one attachment member which is attached through a first seam to a rear portion of the body supporting member and attached through a second seam to a base sheet that covers at least a portion of inclined surface, bed, wheelchair, or the like. The attachment member and said seams are configured so that when the attachment member is extended, the distance between the base sheet and the first portion of the body supporting member is greater than the distance between the base sheet and the second portion of the body supporting member.

32 Claims, 3 Drawing Sheets

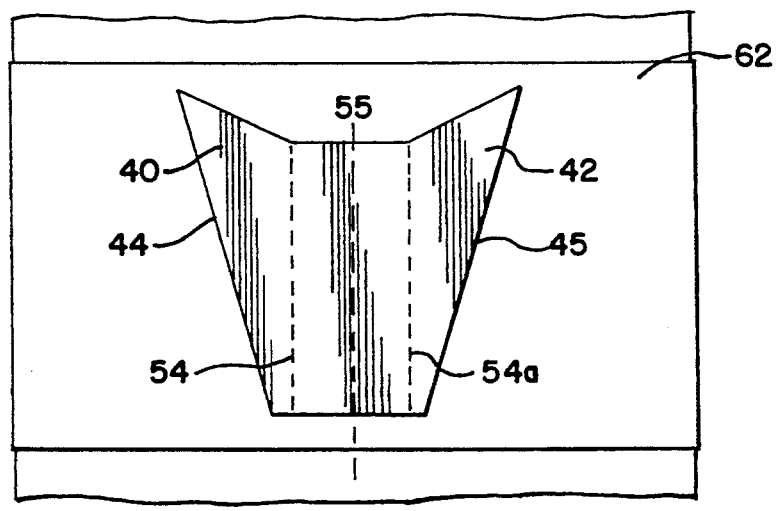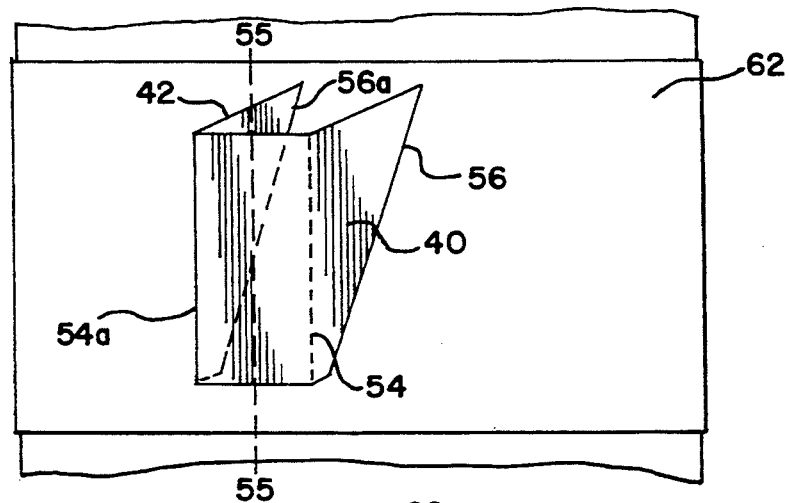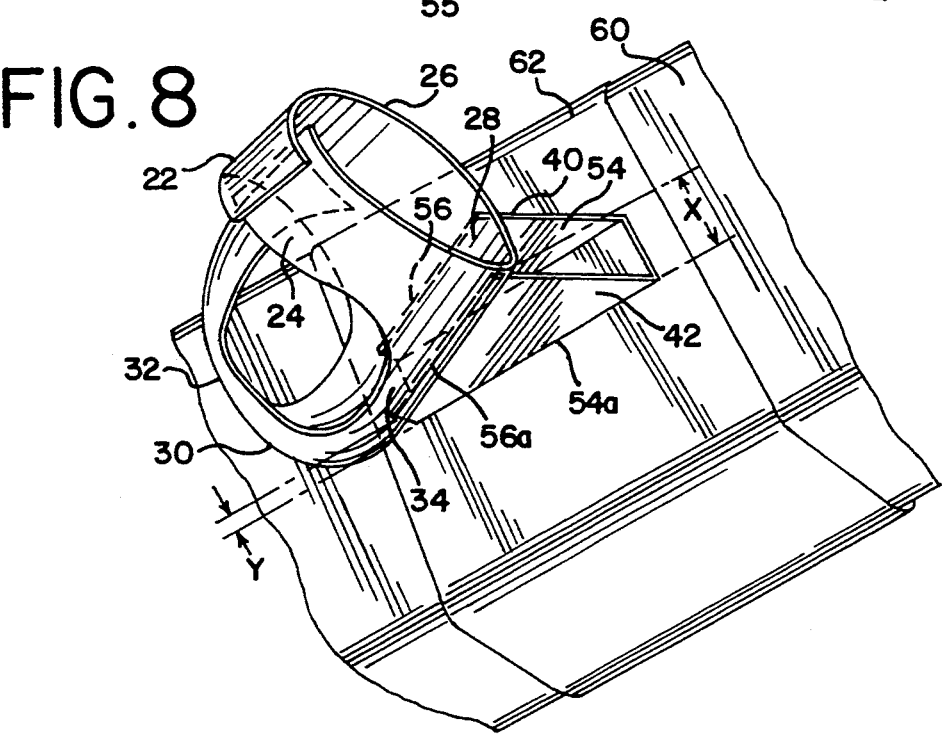

APPARATUS FOR SUPPORT OR POSITIONAL TREATMENT

This specification is a continuation-in-part of application Ser. No. 07/733,722, filed on Jul. 22, 1992, now abandoned.

BACKGROUND OF THE INVENTION

The present invention relates to articles of support for maintaining an individual's body position. More specifically the present invention relates to an article for supporting individuals requiring positional treatment for various illness or physical therapy on an inclined surface, bed, wheelchair, or the like.

Various illnesses and physical therapy treatments often require supporting an individual in an inclined position, for example on a bed, such that the individual does not slip or slide down from their elevated orientation. For example, one such condition which usually affects infants and small children is known as gastroesophageal reflux condition (GER). In treating GER, it is desirable to keep the infant or child supported on a mattress or article of bedding that has an elevated orientation, often of about thirty degrees (30°).

Various types of support, restraint, and harness devices have been developed for holding individuals in a fixed position on a bed.

U.S. Pat. No. 4,657,005 issued on Apr. 14, 1987 to Williamson discloses a GER harness which secures an infant on an inclined surface. The harness includes shoulder and anchor straps and an anti-roll strap.

U.S. Pat. No. 4,860,771 issued on Aug. 29, 1989 to Burgos discloses a reusable hospital sheet for a patient that can be tied to a hospital bed and wrapped around the patient. An opening is provided in the sheet for exiting of tubes from the lower abdomen of the patient.

U.S. Pat. No. 4,911,105 issued on Mar. 27, 1990 to Hocum discloses a harness for restraining a child in bed. The device includes a body harness and a plurality of hold down straps.

U.S. Pat. No. 4,989,286 issued on Feb. 5, 1991 to Tucker discloses a bedding article for supporting infants with gastroesophageal reflux condition which provides a fabric case band that includes an endless band that encircles the mattress with a first closed end adapted to register with an end of the mattress and a second opened lower end portion.

SUMMARY OF THE INVENTION

Briefly stated, the present invention is an article for support of an individual. More specifically, the present invention is an article for supporting individuals requiring positional treatment for various illnesses or physical therapy.

In accordance with the present invention, the article for support includes a body supporting member made of pliable material. The body supporting member has a first portion and a second portion. The first portion is adapted to encircle the waist of the individual and the second portion is adapted to pass through the crotch of the individual.

The article for support further includes an attachment member, which in one preferred embodiment is attached through a first seam to a rear portion of the body supporting member and attached through a second seam to a base sheet covering at least a portion of an inclined surface, bed, or chair. The attachment member and said seams are configured so that when the attachment member is extended, the distance between the base sheet and the first portion, or waist encircling portion, of the body supporting member is greater than the distance between the base sheet and the second portion, or crotch portion, of the body supporting member.

Preferably, the apparatus of the present invention includes a second attachment member which is substantially similar in size and shape as the first attachment member. In this preferred embodiment, the first and second attachment members are attached to the rear of the body supporting member and to the base sheet through a series of parallel spaced apart seams.

In another preferred embodiment, the first and second attachment member are formed from a single quadrilateral-shaped sheet of pliable material and are attached through a series of parallel spaced apart seams to the rear of the body supporting member and to the base sheet. Alternatively, the first and second attachment member are formed from a single trapezium-shaped sheet of pliable material and are attached to the rear of the body supporting member and to the base sheet through a series of parallel spaced apart seams. Alternatively, the first and second attachment member are formed from a single trapezoid-shaped sheet of pliable material and are attached through a series of parallel spaced apart seams to the rear of the body supporting member and to the base sheet.

In another preferred embodiment of the present invention, the article for support is adapted to be used in connection with a surface in which an individual may be positioned upright such as a chair, wheelchair, or stroller. In accordance with this preferred embodiment, the article for support includes a body supporting member and at least one attachment member substantially similar to the previously described preferred embodiments. Also, the base sheet of this preferred embodiment is adapted and configured to cover at least a portion of the upright surface, such that the article for support of the present invention may be used by a person in a chair, wheelchair, stroller or other like device.

The present invention offers several advantages over the prior art. Some examples of such advantages include providing a means of attaching an otherwise comfortable and useful pelvic support to an altered base sheet in such a manner as to maintain a greater level of mobility and movement by the patient than past devices without sacrificing any required level of support or body orientation. Individuals using the present invention are able to sit up or roll onto their side enhancing their comfort. Additionally, by maintaining proper body position without completely restricting the patient's capacity to move, many causes of skin breakdown are reduced. This reduces the risk of complications due to such breakdowns.

Another advantage includes providing this means of pelvic support to a wheelchair or other upright support device such as a stroller. A further advantage of this invention is to allow ease of access to individuals using the present invention.

The present invention, together with its attendant objects and advantages, will be best understood with reference to the detailed description below read in conjunction with the accompanying drawings.

BRIEF DESCRIPTION OF THE DRAWINGS

FIG. 6 is a perspective view of an attachment member of a preferred embodiment of the present invention attached to a section of a base sheet.

FIG. 7 is a perspective view of an attachment member of a preferred embodiment of the present invention attached to a section of a base sheet.

FIG. 8 is a perspective view of a preferred embodiment of the present invention attached to a section of a base sheet.

DETAILED DESCRIPTION OF THE PREFERRED EMBODIMENTS

Figure 1:
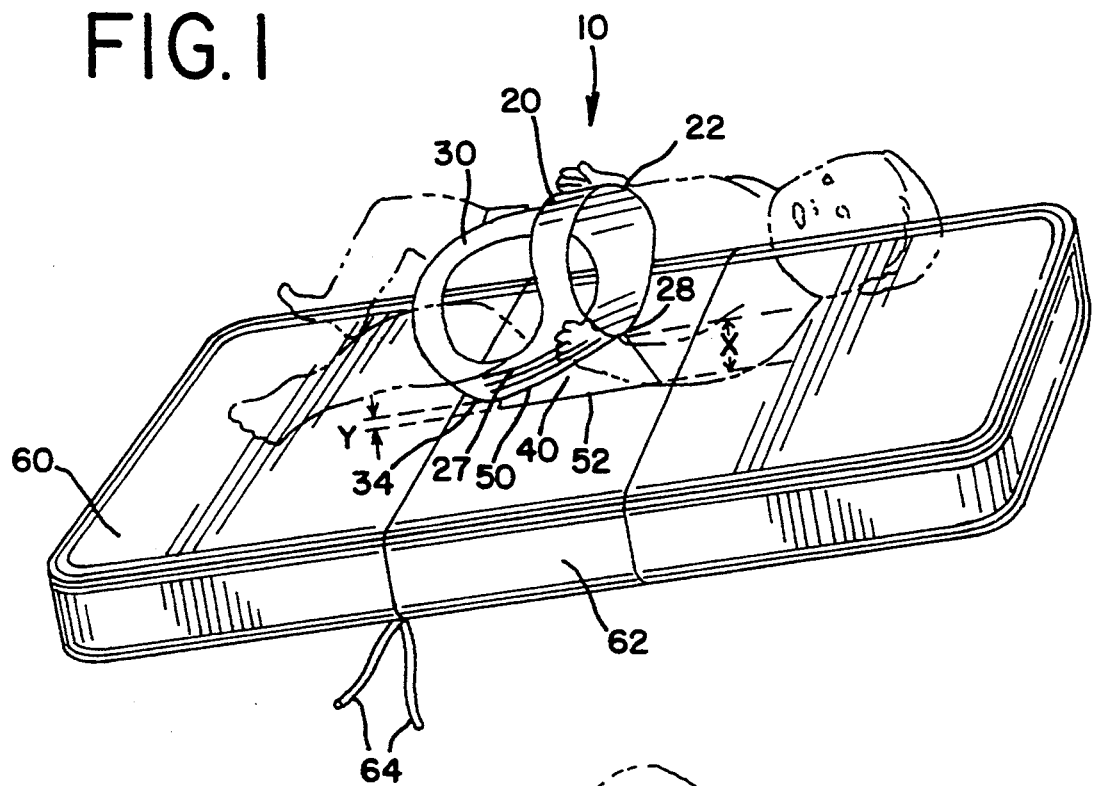
FIG. 1 is a perspective view of the present invention illustrating a preferred use for the present invention.

The apparatus for support of an individual, for example during positional treatment of an individual, is illustrated in FIGS. 1 through 8. Generally, the article for support 10, which may be used for positional treatment, includes a body supporting member 20, as shown in FIG. 1. Preferably, the body supporting member is made of a pliable material with a first portion 22 adapted to encircle the waist of an individual and a second portion 30 adapted to pass through the crotch.

Preferably, the first portion 22 of the body supporting member 20 includes an upper left extension 24 and an upper right extension 26. More preferably, the upper left extension 24 and the upper right extension 26 are configured and adapted to wrap about the waist of an individual and releasably connect to each other, as shown in FIGS. 1 through 5.

Preferably, the second portion 30 of the body supporting member 20 includes a crotch extension 32. More preferably, the crotch extension 32 is adapted and configured to pass through the crotch of an individual and releasably connect to at least one of the upper left 24 or upper right 26 extensions, as shown in FIGS. 1 through 5.

The apparatus also includes an attachment member 40 as illustrated in FIG. 1. Generally the attachment member 40 is also made of a sheet of pliable material. Preferably, this attachment member is attached through a first seam 50 to a rear portion 27 of the body supporting member 20 and through a second seam 52 to a base sheet 60 covering at least a portion of an inclined surface, bed, wheelchair or the like. Preferably, the first seam 50 extends a vertical distance from the rear 28 of the first portion 22 of the body supporting member 20 to the rear 34 of the second portion 30 of the body supporting member 20.

The attachment member 40 and said seams 50 and 52, are configured so that, when the attachment member is extended, the distance X between the base sheet 60 and the rear 28 of the first portion 22, or waist encircling portion, of the body supporting member 20 is a greater distance than the distance Y between the base sheet 60 and the rear 34 of the second portion 30, or crotch portion, of the body supporting member 20.

Figure 3:
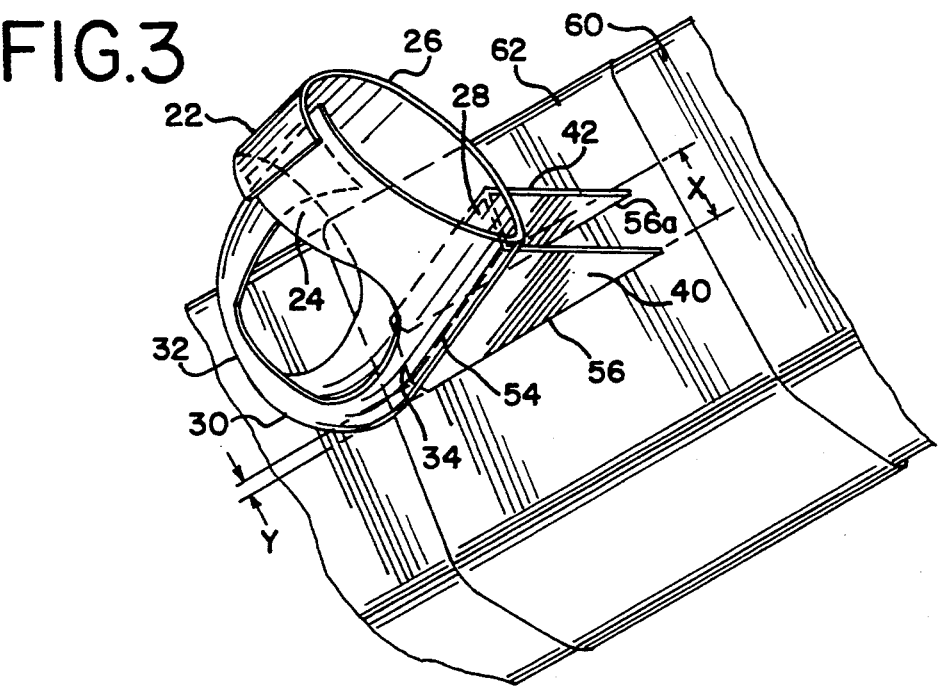
FIG. 3 is a perspective view of a preferred embodiment of the present invention attached to a section of a base sheet.

In another preferred embodiment, the apparatus of the present invention includes a second attachment member 42. Generally, the second attachment member 42 is also made of a pliable material, which is similar or identical to that of the first attachment member 40. Preferably, the second attachment member 42 is configured to be of similar shape and size as that of the first attachment member 40. In this preferred embodiment the first and second attachment members 40 and 42, are attached to the rear 27 of the body supporting member 20 and to the base sheet 60 through a series of at least two parallel seams 54, 54a and 56, 56a which are spaced an equal distance apart along the entire length of the seams 54, 54a and 56, 56a, as illustrated in FIG. 3.

Figure 5:
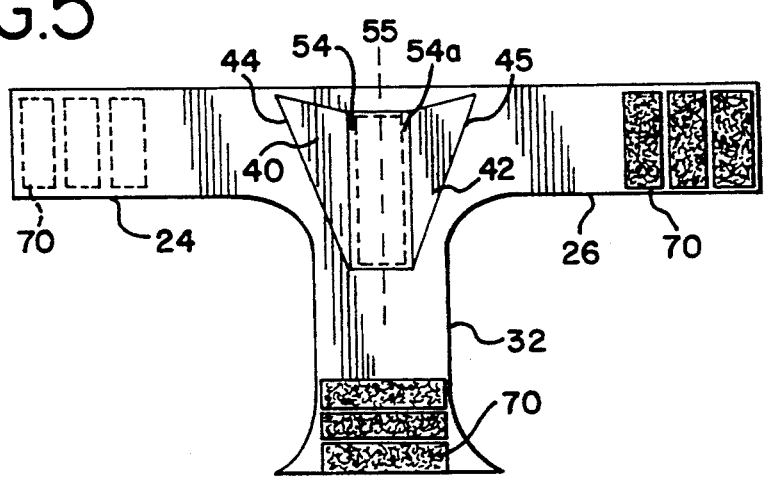
FIG. 5 is a rear view of a preferred embodiment of the present invention.

In another preferred embodiment the first attachment member 40 and the second attachment member 42 are formed from a single sheet of pliable material. Preferably, the single sheet of pliable material is quadrilateral in shape. More preferably, the single sheet of pliable material is trapezium in shape and is attached through parallel spaced apart seams 54, 54a to the rear 27 of the body supporting member 20. The first attachment member 40 being that portion of the sheet of pliable material that extends to the left of the first parallel seam 54 as illustrated in FIG. 5. The second attachment member 42 being that portion of the sheet of pliable material that extends to the right of the second parallel seam 54a, as illustrated in FIG. 5. Preferably, the parallel spaced apart seams 54 and 54a are placed at an equal and opposite distance outward from the centerline 55 of the single sheet of pliable material. Most preferably, the parallel spaced apart seams 54 and 54a attach the sheet of pliable material to the body supporting member 20 such that the first attachment member 40 and second attachment member 42 are of substantially the same size and shape as illustrated in FIG. 5.

In the above discussed preferred embodiments the first and second attachment members 40 and 42 are attached to the base sheet 60 through a second series of parallel spaced apart seams 56 and 56a. Preferably, first attachment member 40 is attached to the base sheet 60 by seam 56 as illustrated in FIG. 3 and 7. Preferably, seam 56 is placed along the length of the outermost non-parallel edge 44 of attachment member 40 from the centerline 55 of the sheet of pliable material as illustrated in FIGS. 3, 5 and 7. Preferably, second attachment member 42 is attached to the base sheet 60 by seam 56a as illustrated in FIGS. 3, 5 and 7. Preferably, seam 56a is placed along the length of the outermost non-parallel edge 45 of attachment member 42 from the centerline 55 of the sheet of pliable material as illustrated in FIGS. 3, 5 and 7.

Alternatively, the first attachment member 40 and the second attachment member 42 may be formed from a single sheet of pliable material that is trapezoidal in shape. In this preferred embodiment, the attachment members 40 and 42 are attached to the rear 27 of the body supporting member 20 through a series of parallel spaced apart seams that are substantially similar to 54 and 54a as illustrated in FIG. 5. In this preferred embodiment the first and second attachment members 40 and 42 are attached to the base sheet 60 through a second series of parallel spaced apart seams substantially similar to seams 56 and 56a as illustrated in FIG. 3 and 7.

In another preferred embodiment, the first attachment member 40 and the second attachment member 42 are formed from a single quadrilateral-shaped sheet of pliable material. More preferably, the sheet of pliable material is trapezium-shaped. However in this preferred embodiment the sheet of pliable material is attached through parallel spaced apart seams 54 and 54a to the base sheet 60, as illustrated in FIGS. 6 and 8.

In this preferred embodiment the first attachment member 40 is once again that portion of the sheet of pliable material that extends to the left of the first parallel seam 54. The second attachment member 42 is that portion of the sheet of pliable material that extends to the right of the second parallel seam 54a, as illustrated in FIG. 6 and 8. Preferably the parallel spaced apart seams 54 and 54a of this embodiment are placed at an equal and opposite distance outward from the centerline 55 of the single sheet of pliable material.

In these preferred embodiments the first and second attachment members 40 and 42 are attached to the rear 27 of the body supporting member 20 through a second series of parallel spaced apart seams 56 and 56a. Preferably, seams 56 and 56a attach the first and second attachment members 40 and 42 to the body supporting member 20. Preferably, seam 56 attaches the first attachment member 40 to the body supporting member 20 along attachment member 40's outermost non-parallel edge 44 extending from the centerline 55 of the sheet of pliable material. Preferably, seam 56a attaches the second attachment member 42 to the body supporting member 20 along attachment member 42's outermost non-parallel edge 45 extending from the centerline 55 of the sheet of pliable material, as illustrated in FIG. 6 and 8. Most preferably, the sheet of pliable material is attached to the base sheet 60 such that the first attachment member 40 and second attachment member 42 are of substantially the same size and shape.

Alternatively, the first attachment member 40 and the second attachment member 42 may be formed from a single trapezoid-shaped sheet of pliable material and attached to the base sheet 60 in substantially the same manner as described above and as illustrated in FIG. 6 and 8. In this preferred embodiment the first and second attachment member 40 and 42 are attached to the body supporting member 20 through a second series of parallel spaced apart seams substantially similar to seams 56 and 56a as described above and illustrated in FIG. 6 and 8.

Figure 2:
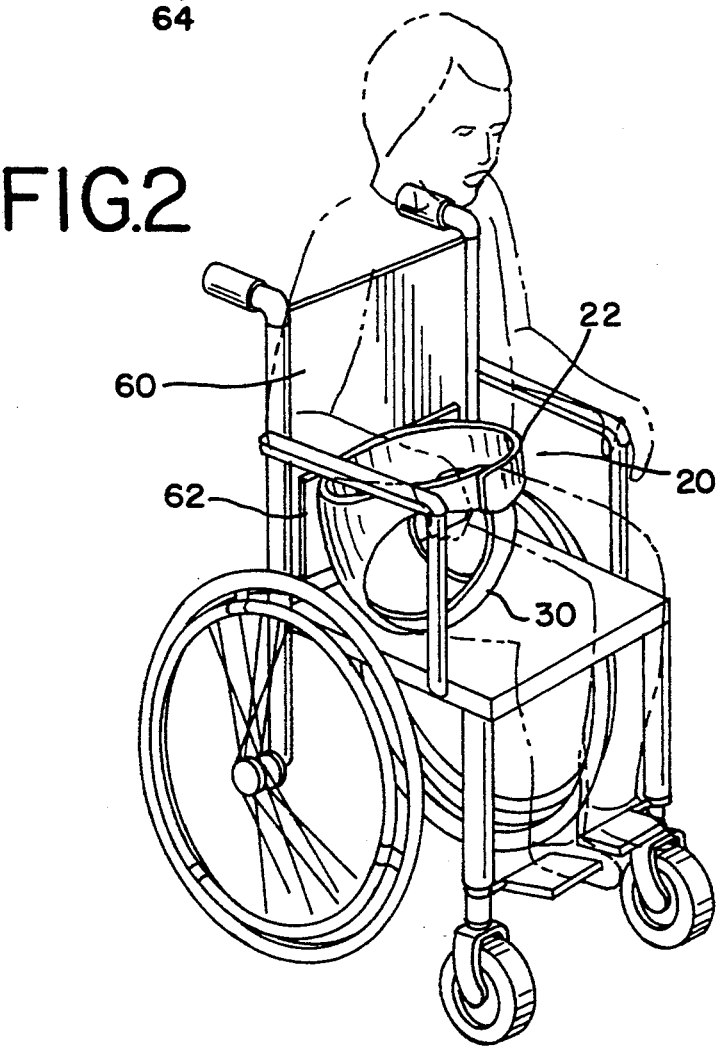
FIG. 2 is a perspective view of the present invention illustrating an alternative preferred use for the present invention.

In another preferred embodiment, the article for support, or positional treatment, of the present invention is adapted and configured to be used in connection with a surface in which an individual may be positioned upright such as a chair, wheelchair, or stroller. In accordance with this preferred embodiment, the article for support of the present invention is substantially similar to the above described embodiments. However, the base sheet of this preferred embodiment is adapted and configured to cover at least a portion of the upright surface such that the article for support of the present invention may be used by a person in a chair, wheelchair, stroller, or other like device. FIG. 2 illustrates this preferred embodiment in which the base sheet is affixed to a wheelchair.

Optionally, the attachment members of the present invention may be releasably attached to either the rear portion 27 of the body supporting member 20, or the base sheet 60, or both.

In those embodiments that include a first and second attachment member, the article for support is configured so that, when each attachment member is extended, the distance X between the base sheet 60 and the rear 28 of the first portion 22, or waist encircling portion, of the body supporting member is a distance greater than the distance Y, which is the distance between the base sheet 60 and the rear 34 of the second portion 30, or the crotch portion, of the body supporting member 20 as illustrated in FIGS. 3 and 8.

Generally, the apparatus 10 of the present invention can be manufactured from any suitable pliable fabric material, such as cotton, flannel, canvass, netting, Lycra ®, or the like, having sufficient structural strength to handle the size and weight of the patient using the device. Cotton or cotton blends are preferred. The material may be machine washable or disposable such as that used in hospital gowns.

Figure 4:
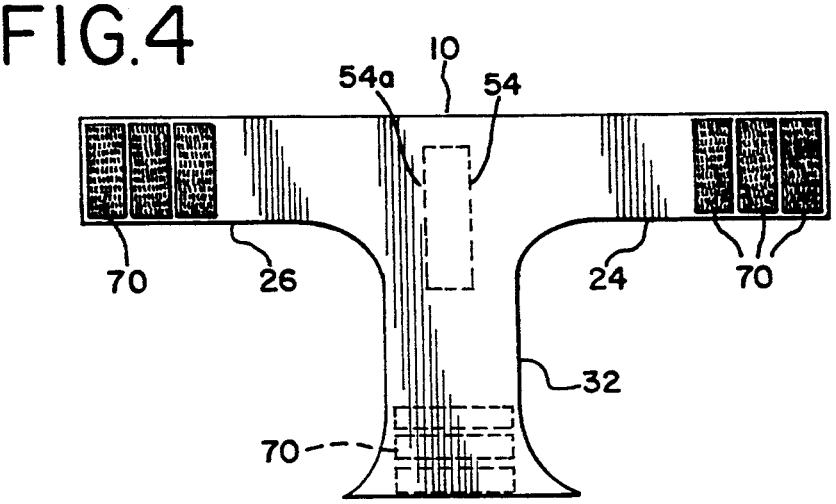
FIG. 4 is a front view of a preferred embodiment of the present invention.

Generally, Velcro ®, clips, hooks, zippers, or other releasable closure methods 70 may be used to releasably fasten the first and second portions of the body supporting member about an individual as illustrated in FIGS. 4 and 5. Velcro ® is preferred. Similar releasable closure methods may be used to releasably fasten one or more attachment members to the rear of the body supporting member, to the base sheet, or both.

Generally, the base sheet 60 of the present invention can be manufactured of any suitable sheet material, such as that described above for the apparatus. Preferably the base sheet 60 is formed of a washable pliable material, such as cotton. More preferably, the base sheet 60 is configured to have a reinforcing band of material 62 at a section of the sheet corresponding to that portion of the sheet where one or more attachment members are affixed. Preferably, the reinforcing band 62 extends laterally the width of the base sheet 60 and extends longitudinally from a point at least above the uppermost point where the attachment member is affixed to at least a point below the lowermost point where the attachment member is affixed, as illustrated in FIGS. 2–3, and 6–8.

Optionally, the base sheet 60 may include a plurality of straps 64 configured to anchor the base sheet 60 to the frame of a bed and aid in preventing lateral motion and slippage of the base sheet 60 caused by an individual's activity.

Optionally, the base sheet 60 of the present invention may be adapted or configured to cover at least a portion of a wheelchair or other surface in which an individual may be positioned upright, such as a stroller for example. In this preferred embodiment, the base sheet 60 may include a reinforcing band 62 and a plurality of straps that are configured to anchor the base sheet 60 to the frame of a wheelchair or other upright surface.

In view of the numerous modifications which could be made to the preferred embodiments disclosed herein without departing from the scope or spirit of the present invention, the details herein are to be interpreted as illustrative and not as limiting. Further, the foregoing description of the preferred embodiments of the present invention has been presented for purposes of illustration and description. They are not intended to be exhaustive or to limit the invention to the precise forms disclosed. Obviously many modifications and variations are possible in light of the above teachings. The embodiments were chosen and described in order to best explain the principles of the invention and various embodiments and with various modifications as are suited to the particular use contemplated. It is intended that the scope of the invention be defined by the appended claims, including all equivalents.

I claim:

1. An apparatus for support of a person on a surface comprising:

a pliable diaper-shaped body supporting member including a torso portion having a torso opening formed therein and a crotch portion having a leg opening for each leg formed therein;

a base sheet for covering at least a portion of the surface; and a flexible attachment member attached to a rear portion of the body supporting member and to said base sheet, said attachment member including a first portion and a second portion, said first and second portion extending between and attached to said rear portion and said base sheet, said first portion having a greater extended length than said second portion for allowing said torso portion to extend a first distance outward from the base sheet and for restricting the crotch portion from extending further than a second distance from the base sheet, which second distance is shorter than the first distance.

2. The apparatus of claim 1 wherein the surface comprises a back support portion of a chair.

3. The apparatus of claim 1 further comprising a second attachment member, said attachment member and said second attachment member being attached to the rear of said body member and to said base sheet through spaced apart generally parallel seams.

4. The apparatus of claim 3 wherein said attachment member and said second attachment member are formed from a single trapezoid-shaped sheet of pliable material with the two non-parallel edges attached through generally parallel spaced apart seams to the rear of the body supporting member.

5. The apparatus of claim 3 wherein said attachment member and said second attachment member are formed from a single trapezoid-shaped sheet of pliable material with the two non-parallel edges attached through generally parallel spaced apart seams to the base sheet.

6. The apparatus of claim 2 wherein said torso portion has an upper right extension and an upper left extension, said extensions adapted to wrap around the torso and releasably connect to each other.

7. The apparatus of claim 6 wherein said crotch portion has a crotch extension for passing through the crotch and releasably connecting to at least one of said upper extensions.

8. The apparatus of claim 1 wherein said attachment member is releasably attached to said base sheet.

9. The apparatus of claim 1 wherein said attachment member is releasably attached to said body member.

10. The apparatus of claim 1 wherein said surface is inclined.

11. The apparatus of claim 1 wherein the attachment member is a flexible sheet having a top and bottom portion, a first edge of said flexible sheet attached to said base sheet and a second edge of said flexible sheet attached to said body, said top portion attached to an upper region of the torso portion and said bottom portion attached below said top portion, said top portion having a greater length than said bottom portion for allowing said torso portion to extend a greater distance from the base than the crotch portion.

12. An apparatus for support of a person on an inclined surface comprising:

a diaper-shaped body supporting member of pliable material including a waist portion for encircling the waist and a crotch portion formed beneath the waist portion for covering at least a portion of the crotch;

a base sheet for covering at least a portion of the inclined surface;

a flexible attachment member attached to a rear portion of the body supporting member and to said base sheet, said attachment member including an upper portion and a lower portion, said upper portion attached to a top region of said waist portion and said lower portion attached to a body member area below said top region, said upper portion and lower portion extending between and attached to said rear portion and said base sheet, said upper portion having a greater extended length than said lower portion for allowing said waist portion to extend outward from the base sheet and for restricting said crotch portion from extending a further distance than the waist portion from the base sheet.

13. The apparatus of claim 12 wherein said attachment member comprises a right and left attachment member, said right attachment member comprised of a sheet of pliable cloth, said right attachment member being attached to a right side of a rear portion of the body supporting member and to said base sheet, said left attachment member comprised of a sheet of pliable cloth, said left attachment member being attached to a left side of a rear portion of the body supporting member and to said base sheet.

14. The apparatus of claim 12 wherein said inclined surface is a back support portion of a chair.

15. The apparatus of claim 12 wherein said waist portion having an upper right extension member and an upper left extension member for wrapping around the waist and attaching to each other.

16. The apparatus of claim 13 wherein said crotch portion having a crotch extension portion for passing through the crotch and attaching to at least one of said upper extensions.

17. An apparatus for support of a person on an inclined surface comprising:

a diaper-shaped body supporting member of pliable material including a waist encircling portion for encircling the waist and a crotch portion for passing through the crotch and providing an opening for each leg between the crotch portion and waist encircling portion, said crotch portion extending from a lower center region of said waist encircling portion;

a base sheet for covering at least a portion of the inclined surface; and an attachment member comprised of a sheet of pliable material including an upper and a lower portion, said attachment member being attached to a rear portion of the body supporting member and to said base sheet, said upper portion attached to said waist encircling portion and said lower portion attached to said crotch portion, said upper portion and lower portion extending between and attached to said rear portion and said base sheet, said upper portion having a greater extended length than said lower portion for allowing said waist encircling portion to extend outward from said base sheet and for preventing said crotch portion from extending a further distance than the waist encircling portion from the base sheet.

18. The apparatus of claim 17 further comprising a second attachment member of similar shape and size to said attachment member, said attachment member and said second attachment member attached to the rear portion of said body supporting member and to said base sheet through spaced apart generally parallel seams.

19. The apparatus of claim 18 wherein said attachment member and said second attachment member are formed from a single trapezoid-shaped sheet of pliable material with the two non-parallel edges attached through generally parallel spaced apart seams to the rear portion of said body supporting member.

20. The apparatus of claim 18 wherein said attachment member and said second attachment member are formed from a single trapezoid-shaped sheet of pliable material with the two non-parallel edges attached through generally parallel spaced apart seams to the base sheet.

21. The apparatus of claim 17 wherein the body supporting member has an upper right extension and an upper left extension for wrapping around the waist and releasably connecting to each other.

22. The apparatus of claim 21 wherein said body supporting member further includes a crotch extension for passing through the crotch and releasably connecting to at least one of said upper extensions.

23. The apparatus of claim 17 wherein the attachment member is releasably attached to said base sheet.

24. The apparatus of claim 17 wherein the attachment member is releasably attached to the rear potion of said body supporting member.

25. The apparatus of claim 17 wherein said inclined surface is a back support portion of a chair.

26. The apparatus of claim 17 wherein said body supporting member is cloth.

27. The apparatus of claim 17 wherein said base sheet is adapted to cover at least a back support portion of a wheelchair.

28. An apparatus for support of a person on an inclined surface comprising:
a diaper-shaped body supporting member of pliable material including a first portion for encircling the waist and a second portion for passing through the crotch, said second portion extending at one end from a lower rear center region of said first portion and attached at a second end to a front region of the first portion;
a base sheet for covering at least a portion of the surface;
a right attachment member comprised of a sheet of pliable cloth, said right attachment member being attached through a right first seam to a right side of a rear portion of the body supporting member and through a right second seam to said base sheet; and
a left attachment member comprised of a sheet of pliable cloth, said left attachment member being attached through a left first seam to a left side of a rear portion of the body supporting member and through a left second seam to said base sheet, said attachment members each including an upper portion and a lower portion, said upper portion attached to said first portion and said lower portion attached to said second portion, said upper portion having a greater extended length than said lower portion for allowing said first portion to extend outward from said base sheet and for preventing the second portion from extending a further distance than the first portion from the base sheet, said right seams being spaced apart from and generally parallel to said left seams.

29. The apparatus of claim 28 wherein said first portion of said body supporting member includes an upper left extension and an upper right extension for wrapping about the waist and releasably attaching to each other.

30. The apparatus of claim 29 wherein said second portion of said body supporting member has a crotch extension for passing through the crotch and releasably attaching to at least one of said upper extensions.

31. The apparatus of claim 28 wherein the body supporting member is cloth.

32. The apparatus of claim 28 wherein the inclined surface is a back support portion of a wheelchair.

* * * * *